United States Patent
Neuser et al.

(10) Patent No.: US 10,194,874 B2
(45) Date of Patent: Feb. 5, 2019

(54) COMPUTED TOMOGRAPHY METHOD, COMPUTER SOFTWARE, COMPUTING DEVICE AND COMPUTED TOMOGRAPHY SYSTEM FOR DETERMINING A VOLUMETRIC REPRESENTATION OF A SAMPLE

(75) Inventors: Eberhard Neuser, Wunstorf (DE); Alexander Suppes, Garbsen (DE); Nils Rothe, Hannover (DE); Michael Hoetter, Gehrden (DE); Anja Frost, Bremen (DE)

(73) Assignee: GE SENSING & INSPECTION TECHNOLOGIES GMBH, Huerth (DE)

( * ) Notice: Subject to any disclaimer, the term of this patent is extended or adjusted under 35 U.S.C. 154(b) by 4 days.

(21) Appl. No.: 13/805,971

(22) PCT Filed: May 27, 2011

(86) PCT No.: PCT/EP2011/002628
§ 371 (c)(1),
(2), (4) Date: Mar. 12, 2014

(87) PCT Pub. No.: WO2012/163367
PCT Pub. Date: Dec. 6, 2012

(65) Prior Publication Data
US 2014/0185897 A1   Jul. 3, 2014

(51) Int. Cl.
*A61B 6/00* (2006.01)
*A61B 6/03* (2006.01)
(Continued)

(52) U.S. Cl.
CPC .......... *A61B 6/032* (2013.01); *A61B 6/5247* (2013.01); *G06T 7/38* (2017.01); *G06T 11/008* (2013.01);
(Continued)

(58) Field of Classification Search
CPC ... G06K 9/6288; G06T 7/0012; G06T 11/006; G06T 2207/10116; G06T 2207/30004;
(Continued)

(56) References Cited

U.S. PATENT DOCUMENTS 5,671,265 A * 9/1997 Andress ............... 378/98.11
6,904,117 B2   6/2005 Hein et al.
(Continued)

FOREIGN PATENT DOCUMENTS

WO   WO-2000-025268   5/2000
WO   WO-2011-015957   2/2011
WO   WO-2011-036624   3/2011

OTHER PUBLICATIONS

Ben Brahim et al., Solving Data Fusion Problems Using Robust Classifiers Combination, Dec. 7-10, 2010 [retrieved Jan. 25, 2017], 2010 International Conference of Soft Computing and Pattern Recognition, pp. 303-308. Retrieved from the Internet: http://ieeexplore.ieee.org/abstract/document/5686639/.*
(Continued)

*Primary Examiner* — Andrew Moyer
*Assistant Examiner* — Dennis Rosario
(74) *Attorney, Agent, or Firm* — Mintz Levin Cohn Ferris Glovsky and Popeo, P.C.

(57) ABSTRACT

A method of using computed tomography for determining a volumetric representation of a sample, involving a first reconstruction for reconstructing first reconstructed volume data of the sample from first x-ray projection data of the sample taken by an x-ray system, a second reconstruction for reconstructing second reconstructed volume data of the sample from second x-ray projection data of the sample taken by an x-ray system, characterized by calculating first individual confidence measures for single voxels of the first reconstructed volume data, calculating second individual
(Continued)

confidence measures for single voxels of the second reconstructed volume data, and calculating, in a subsequent step, at least one resulting set of individual values for each voxel based on the first individual confidence measures and the second individual confidence measures.

12 Claims, 3 Drawing Sheets

(51) Int. Cl.
*G06T 7/38* (2017.01)
*G06T 11/00* (2006.01)

(52) U.S. Cl.
CPC .............. *G06T 2207/10081* (2013.01); *G06T 2207/20221* (2013.01)

(58) Field of Classification Search
CPC ............ G06T 2207/10081; G06T 5/50; G06T 2207/10072; G06T 2207/10088; G06T 7/30; G06T 2207/20221; G06T 17/00; G06T 2207/20076; G06T 11/003; A61B 5/055; A61B 6/032; A61B 6/037; A61B 34/10; A61B 6/5247; A61B 6/5235; A61B 5/0035; A61B 2090/364; A61B 6/4417
See application file for complete search history.

(56) References Cited

U.S. PATENT DOCUMENTS

| | | | | |
|---|---|---|---|---|
| 7,151,466 B2* | 12/2006 | Gabelmann | ............... | G01V 3/34 340/854.6 |
| 7,308,077 B2* | 12/2007 | Bijjani | ................ | G01N 23/046 378/57 |
| 7,653,263 B2* | 1/2010 | Wheeler | ................ | G06T 7/001 382/294 |
| 8,422,826 B2* | 4/2013 | Holt | ........................ | G06T 5/50 345/634 |
| 8,526,570 B2 | 9/2013 | Neuser et al. | | |
| 8,977,022 B2* | 3/2015 | Neuser | ................ | G06F 19/321 382/128 |
| 2003/0191610 A1 | 10/2003 | Chen et al. | | |
| 2004/0017892 A1 | 1/2004 | Sabol et al. | | |
| 2006/0210131 A1* | 9/2006 | Wheeler, Jr. | .......... | G06T 11/008 382/128 |
| 2008/0234578 A1* | 9/2008 | Claus | .................... | A61B 6/037 600/437 |
| 2009/0136112 A1* | 5/2009 | Bismuth | ................ | G06T 5/002 382/132 |
| 2012/0207359 A1* | 8/2012 | Konukoglu | ............... | G06T 7/35 382/128 |
| 2013/0243298 A1* | 9/2013 | Bredno et al. | ................ | 382/131 |

OTHER PUBLICATIONS

Breve et al., Combining Methods to Stabilize and Increase Performance of Neural Network-Based Classifiers, Oct. 9-12, 2005 [retrieved Sep. 10, 2017], 18th Brazilian Symposium on Computer Graphics and Image Processing, 7 total pages. Retrieved from the Internet: http://ieeexplore.ieee.org/document/1599090/#full-text-section.*

Merrell et al., Real-Time Visibility-Based Fusion of Depth Maps, Oct. 14-21, 2007[retrieved Aug. 27, 2018], 2007 IEEE 11th International Conference on Computer Vision, 8 pages total. Retrieved from the Internet: https://ieeexplore.ieee.org/abstract/document/4408984/.*

Chen et al., "Evidential reasoning based on Dempster-Shafer theory and its application to medical image analysis", Neural and Stochastic Methods in Image and Signal Processing II, pp. 35-46, Oct. 29, 1993.

* cited by examiner

COMPUTED TOMOGRAPHY METHOD, COMPUTER SOFTWARE, COMPUTING DEVICE AND COMPUTED TOMOGRAPHY SYSTEM FOR DETERMINING A VOLUMETRIC REPRESENTATION OF A SAMPLE

CROSS-REFERENCE TO RELATED APPLICATION

The present application is the U.S. National Stage Application of International Patent Application No. PCT/EP2011/002628, filed on May 27, 2011, which is hereby incorporated by reference herein in its entirety, including any figures, tables, or drawings.

The invention relates to a computed tomography method according to the preamble of claim 1, a computer software, a computing device and a computed tomography system.

It is a general demand in computed tomography to suppress the influence of artefacts on the measurement, and to improve the overall quality of the reconstructed volume data.

Different techniques exist for reconstruction of projection data in the field of X-ray compute tomography, among them analytical methods like Feldkamp or helical reconstruction, algebraic methods like ART, SART, SMART, or statistical methods like maximum likelihood reconstruction. However, all of them have their specific advantages and disadvantages. Therefore, different reconstruction techniques may yield different reconstructed density values in certain volume regions, in particular under critical acquisition conditions. A reconstruction method which combines all advantages under all conditions and for all kinds of samples is not known.

Furthermore, it would often be useful to have knowledge about critical regions in the reconstructed volume for example in automated defect recognition, indicating for example that special attention of an inspector or an inspection system is required. A critical region may in particular be a region where the reliability of information about the data quality is questionable or reduced.

Thus, the object of the invention is to provide a computed tomography method and system yielding a higher overall volume data quality and preferably providing information about critical regions in the reconstructed volume. According to an aspect of the invention, another object may be to combine advantages of different reconstruction methods.

The invention solves this object with the features of the independent claims. By reconstructing two different sets of volume data of the sample under varying conditions, calculating corresponding sets of individual confidence measures for both reconstructed volumes, and calculating at least one resulting set of individual values for each voxel based on the first and second individual confidence measures, preferably in a voxel-by-voxel manner, it is possible to obtain detailed information how the reconstruction quality depends on variations of the reconstruction conditions or methods. Such information can advantageously be used in CT volume reconstruction. In particular it can be used for identifying critical regions of the sample which may require special attention or investigation, and which may preferably be displayed to an operator on a display means. Furthermore, the individual confidence measures can be used to identify reconstruction conditions which are preferred in view of the reconstruction data quality and suppression of artefacts.

Preferably a conflict measure is calculated for individual voxels of the sample volume indicating consistency conflicts between each first reconstructed voxel value and the corresponding second reconstructed voxel value. For example, the conflict measure of a voxel may be calculated to become high if the difference between the first and second voxel value is relatively large and both voxel values have a relatively high confidence measure. Regions of the reconstructed sample volume having a high conflict measure, for example a conflict measure exceeding a predetermined threshold, may be identified as critical regions which may require special attention or investigation, and which may preferably be displayed to an operator on a display means. Thus, the conflict measures allow to detect, and preferably visualize, volume elements with contradictory or inexact density values in the reconstructed volume data.

In a preferred application, a fusion step of generating resulting reconstructed volume data based on said comparison of said first and second individual confidence measures is provided. The fusion is preferably executed on a voxel-by-voxel comparison of the first and second individual confidence measures. This can lead to an overall improved data quality of the resulting reconstructed volume because the respective high-quality regions or pixels can be taken from each reconstructed data set, while dismissing the respective low-quality regions or pixels.

The fusion can be executed in different manners. In a preferred embodiment, the fusion is based on Dempster-Shafer-theory. In another simple embodiment, the individual confidence measures are used as weights for the respective reconstructed volume data voxels. Alternatively, for example, for each voxel the value having the higher or highest confidence measure can be chosen as the resulting voxel value, whereas the other value having a lower confidence is dismissed. Other suited fusion schemes are possible.

Preferably a step of calculating individual resulting confidence measures for said reconstructed volume data from said first and second individual confidence measures is provided. The resulting confidence measures can advantageously be used in further reconstruction steps and/or after the reconstruction, for example in a subsequent automated defect recognition procedure. The resulting confidence measures may be calculated in different manners. In a preferred embodiment it may be calculated using the Dempster-Shafer-Theory from the first and second confidence measures. Alternatively, for example, it may be calculated from the first and second individual confidence measures using an error propagation method. Other suited methods of calculating the resulting confidence measure from the first and second confidence measures are possible.

In a preferred embodiment, different reconstruction methods and/or different reconstruction parameter sets are used for said first and second reconstruction step. In this case, the first and second projection data may advantageously be identical. Thus, for each pixel or region of the sample volume the reconstruction method and/or parameter set providing the best reconstruction quality can be used. In this manner, the advantages of different reconstruction methods and/or different reconstruction parameter sets can be combined while avoiding the respective disadvantages.

However, the invention is not limited to varying the reconstruction methods and/or reconstruction parameters. Alternatively, for example, different sets of x-ray projection data obtained by different measurement methods or set-ups of the x-ray system may be used to obtain the first and second reconstructed volume data sets. In this case, the first reconstruction method may advantageously be identical to the second reconstruction method, and/or the first parameter set may advantageously be identical to the second parameter set.

Preferably the confidence measures are calculated from process data of the reconstruction, i.e. from data used in the data stream of the reconstruction process between the x-ray projections and the reconstructed volume data, including the reconstructed volume data and the measured x-ray projections. In particular, no external data, particularly no pre-stored ideal data of ideal samples or data from a sample database, have to be used in the calculation of the confidence measures. Due to this feature the reconstructed volume data do not have to be warped into alignment with ideal volume data with a corresponding inaccuracy, but each individual confidence measure can be exactly and correctly assigned to the corresponding single voxel of the reconstructed volume data. In a preferred embodiment the confidence measures are calculated from the corresponding x-ray projection data and/or the corresponding reconstructed volume data; for example, the first confidence measures are calculated from the first x-ray projection data and/or the first reconstructed volume data. However, it may also be possible to calculate the confidence measures from stored prior knowledge, for example from an ideal sample.

A confidence measure, or quality measure, of a particular voxel is a value unambiguously related to the probability that the density value of that voxel is correct, or that it is equal to a pre-defined density value. Alternatively the confidence measure may be related to the variance of the voxel density, the probability that the density value of that voxel is incorrect, an error in the voxel density, deviation to the true density, or the voxel accuracy. The confidence measure of a voxel gives quantitative information about the quality of the reconstructed voxel density. The entity of confidence measures over all voxels results in a confidence measure distribution, or confidence measure map, for the whole reconstructed sample volume.

The invention is not restricted to a particular reconstruction technique. Possible techniques comprise for example analytical methods like Feldkamp or helical reconstruction, algebraic methods like ART, SART, SMART and statistical methods, for example maximum likelihood reconstruction.

In the following the invention is described on the basis of preferred embodiments with reference to the accompanying drawings, wherein.

Figure 1:
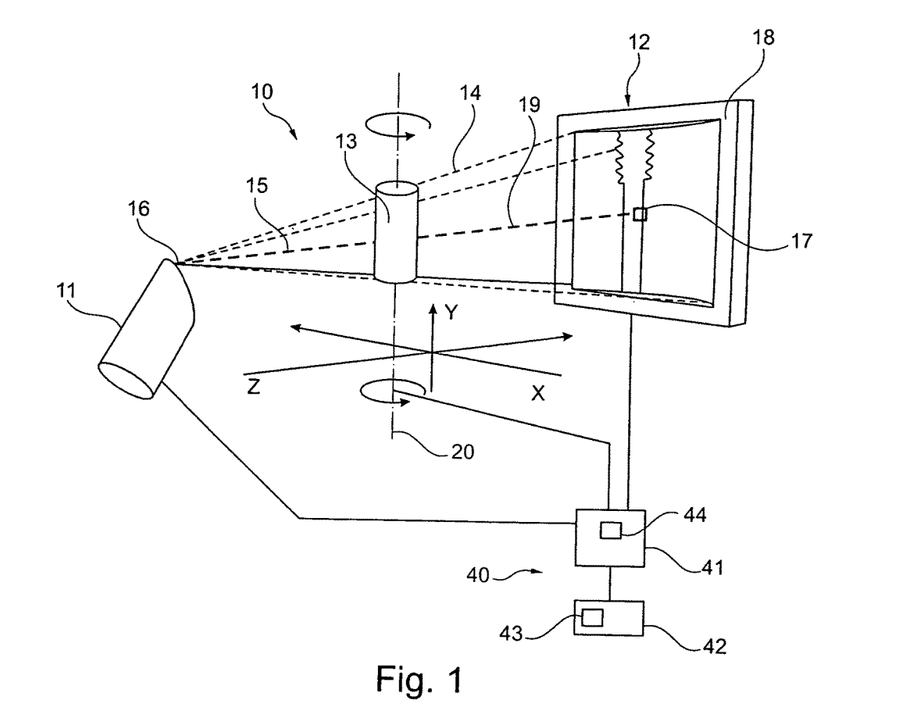
FIG. 1 is a schematic illustration of a computed tomography system.

The computed tomography system shown in FIG. 1 comprises an x-ray system 10 arranged to take a set of x-ray projections of a sample 13. Therefore, the x-ray system 10 comprises an x-ray source 11, in particular an x-ray tube, emitting an x-ray cone 14, an imaging device 12, in particular an x-ray detector, and a sample manipulator 20 which is preferably adapted to rotate the sample 13 around a vertical axis. The x-ray detector 12 in the present example is a two-dimensional detector, however it is also possible to use a one-dimensional detector. A set of x-ray projections of the sample 13 around the full 360° are taken by step-wise rotating the manipulator around a predetermined small angular step and taking an x-ray projection at every rotation angle. An x-ray projection 18, an example of which is shown in FIG. 1, is a one- or two-dimensional image where the measured density value $y_i$ of the i-th pixel 17 represents the attenuation of the corresponding x-ray 15 from the focal spot 16 of the source 11 through the sample 13 resulting in a corresponding attenuated x-ray 19 to the pixel 17 under consideration. Therefore, $y_i = \int v(l) \, dl$ where $v(l)$ represents the density of the sample 13 along the path of the x-ray 15 through the volume of the sample 13. The value $y_i$ may typically be a grey value. The aim of the reconstruction is to find the densities $v_n$ of all voxels of the sample volume to be reconstructed, using the following relation of the densities $v_j$ along the path of an x-ray 15 through the sample 13 to the measured value $y_i$ for this x-ray: $y_i = \Sigma_j w_{ij} v_j$ where $w_{ij}$ are weights denoting the relative contribution of the material density $v_j$ in the voxel j to the measured value $y_i$. In general a set of x-ray projections 21 of a sample 13 is a plurality of x-ray projections 18 taken from different directions, which contains sufficient information to allow reconstruction of the volume structure of the full sample volume by a suited reconstruction technique.

The x-ray system 10 is not limited to rotating a sample holder 20 around a vertical axis. A set of x-ray projections may for example alternatively be obtained by rotating the x-ray system 10 around the fixed sample 13. In general the x-ray system 10 and the sample 13 are suitably movable relative to each other, which may include rotation about one or more vertical and/or horizontal axes for taking a set of x-ray projections. Alternative CT approaches like a tilted rotation axis (<90°) with respect to the beam axis and/or techniques not using a full 360° rotation for taking the set of projections and/or setups with a non constant magnification during taking a set of x-ray projections are possible.

The x-ray projections are read out from the imaging device 12 and sent to a computer apparatus 40 where they are stored in a memory 44 for subsequent evaluation and further processing. The computer apparatus 40 comprises a programmable computing device 41 in particular including a micro-processor or a programmable logic controller, and a user terminal 42 comprising a display device 43. The computing device 40 is programmed with a software for executing the computed tomography method which will be described in the following with reference to FIG. 2. Alternatively a separate computer unit may be used to evaluate the x-ray projections taken with the x-ray system 10.

In the embodiment shown in FIG. 1, the computing device 41 is arranged to control the x-ray system 10, in particular the x-ray source 11 and the sample manipulator 20 for taking the x-ray projections 18 of the sample 13. Alternatively a separate control unit may be used to control the x-ray system 10 for taking the x-ray projections 18 of the sample 13.

Figure 2:
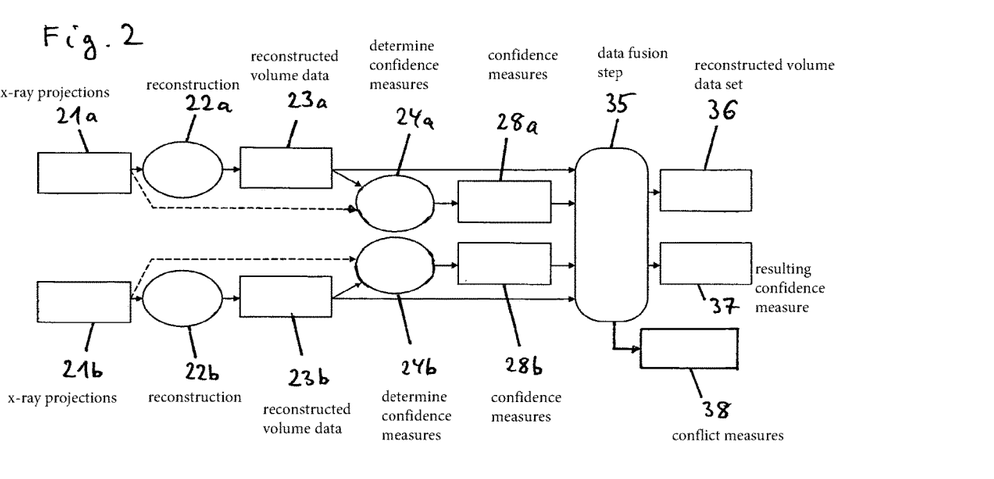
FIG. 2 is a flow diagram illustrating a computed tomography method.

In the computing device 41 a first set of x-ray projections 21a taken from the sample 13 with the x-ray system 10 is input to a first CT reconstruction algorithm 22a. The reconstruction algorithm 22a is adapted to compute first reconstructed volume data 23a of the sample 13. Similarly, a second set of x-ray projections 21b taken from the sample 13 with the x-ray system 10 is input to a second CT reconstruction algorithm 22b which is adapted to compute second reconstructed volume data 23b of the sample 13.

Figure 4:
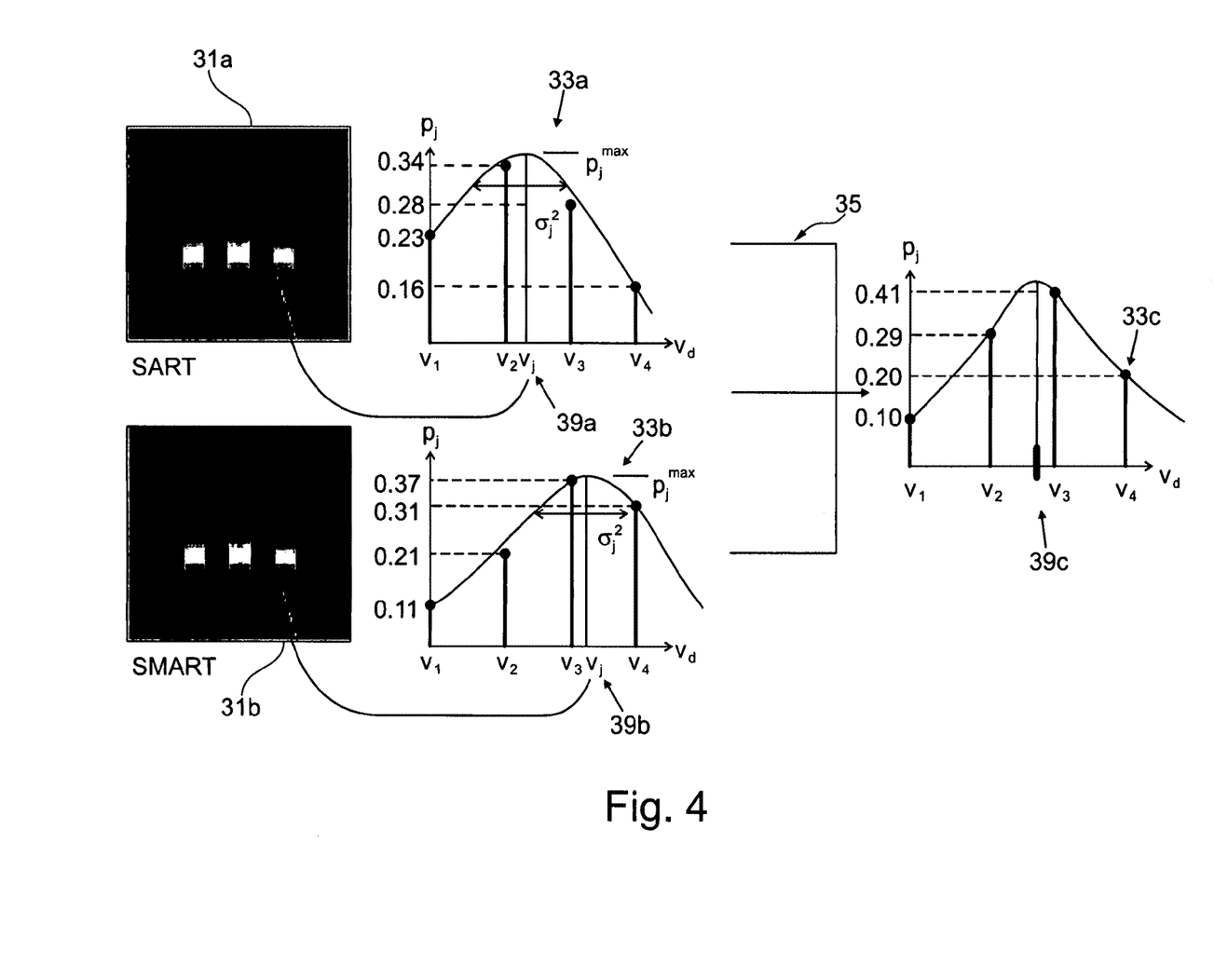
FIG. 4 is schematic illustration of a combination of two different reconstruction techniques.

The first and second reconstructed volume data 23a, 23b originate from the same sample 13 but differ from each other due to variations in the data recording step, leading already to different projection data sets 21a, 21b, and/or the reconstruction 22a, 22b. In one embodiment, the reconstruction 22a may use a first reconstruction method and the reconstruction 22b may use a different second reconstruction method. In the example of FIG. 4 the reconstruction 22a is based on SART reconstruction and the reconstruction 22b is based on SMART reconstruction, leading to different reconstructed volume data as exemplified by the different reconstructed volume data slices 31a, 31b in FIG. 4.

In another embodiment, the reconstruction methods used in 22a, 22b may be the same but different parameters settings are used in the reconstruction. Of course it is also possible to use different reconstruction techniques and different parameter settings.

In still other embodiments, the reconstruction techniques and parameter settings used in the reconstruction 22a, 22b may be identical but different projection data sets 21a, 21b are input. Different projection data sets 21a, 21b may be generated for example by different sample orientations, different scanning trajectories or different x-ray parameters like different x-ray energies. Of course it is also possible to use different reconstruction 22a, 22b and different projection data sets 21a, 21b.

Figure 3:
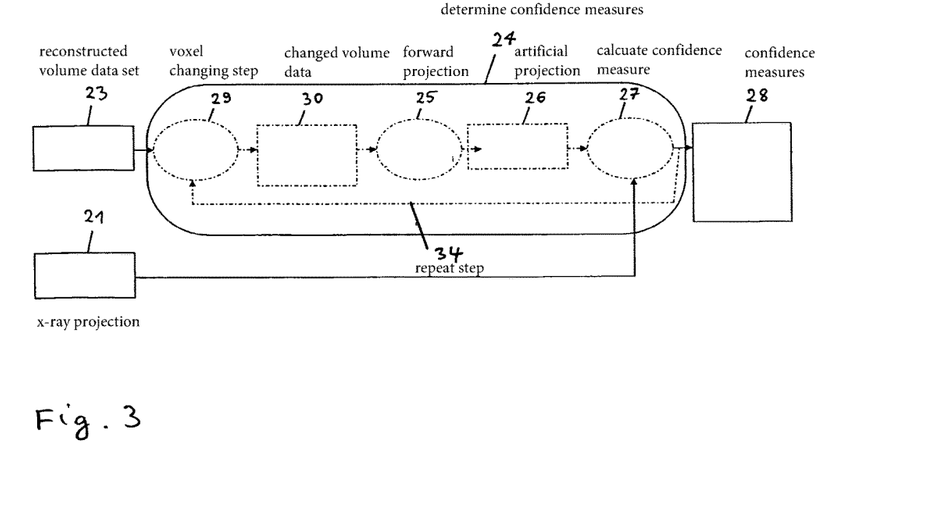
FIG. 3 is a flow diagram illustrating a part of the CT method shown in FIG. 2 relating to calculating confidence measures.

In each reconstructed volume data set 23a, 23b the value $v_n$ of each voxel or volume element represents the attenuation coefficient or density in the corresponding n-th volume element of the sample 13. A complete volume data set 23a, 23b of a sample 13 is given by a set of subsequent volume slices through the whole sample 13. The reconstruction algorithm 22a, 22b is known per se and may be based on any suitable mathematical method, including but not limited to analytical methods like for example Feldkamp or helical reconstruction, iterative methods like algebraic methods, for example ART, SART, SMART etc., or statistical methods, for example maximum likelihood, etc. An example of a reconstructed volume slice 31 of a particular sample is shown in FIG. 3.

For each set of reconstructed volume data 23a, 23b and the corresponding x-ray projections 21a, 21b of the sample 13 under inspection, a process 24a, 24b of determining a corresponding set of confidence measures 28a, 28b of the reconstructed volume data 23a, 23b is carried out. This may be done in the computing device 41 or alternatively in an independent computing device.

The calculation of confidence measures 28a, 28b is described in detail with respect to FIG. 3 in the following. In one embodiment, in which the step 29 and the element 30 to be described later are absent in FIG. 3, an artificial projection, in particular a forward projection 25 is applied to the reconstructed volume slices 23 for generating artificial projections 26 of the sample 13. The forward projection 25 is a mathematical method which simulates the x-ray system 10 shown in FIG. 1 using geometric projection models of a scanner, taking into account the geometry of the x-ray system 10 shown in FIG. 1 in order to make the artificial projections 26 comparable to the x-ray projections 21 recorded with the x-ray system 10. The artificial projections 26 are one- or two-dimensional artificially computed images each consisting of a plurality of pixels.

Figure 5:
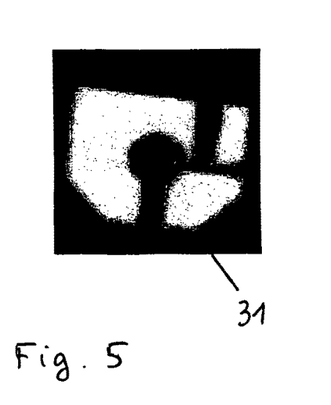
FIG. 5 is a reconstructed volume slice of a sample.
Figure 6:
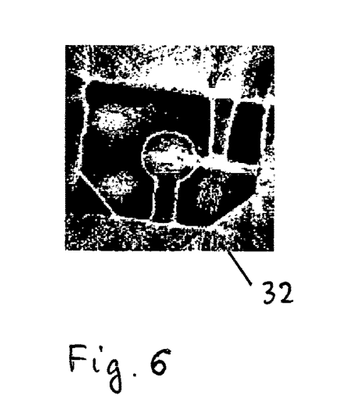
FIG. 6 is a confidence measure slice of the volume slice shown in FIG. 5.

Based on a comparison between the artificial projections 26 and the x-ray projections 21 recorded with the x-ray system 10, individual confidence measures, or quality measures, for each voxel of the reconstructed volume data 23 are then calculated in a confidence measure calculating step 27. In FIG. 6 an example of a confidence measure slice, namely the confidence measure set over the volume slice of FIG. 5, is shown, where black pixels correspond to voxels with high confidence and white pixels correspond to voxels with low confidence.

In more detail, the confidence measure of a voxel may be calculated as follows. For each x-ray projection of the set of real projections 21, i.e. for each x-ray travelling through a particular voxel, the difference $y_i - \Sigma_n w_{in} v_n$ between the contribution $y_i$ of this x-ray projection to the voxel j under inspection and the contribution $\Sigma_n w_{in} v_n$ from a corresponding artificial projection to the voxel j under inspection is calculated. The confidence measure of the voxel under inspection may then be calculated from an absolute density deviation (error) of the voxel under consideration as a sum over terms involving the differences $y_i - \Sigma_n w_{in} v_n$. Absolute density deviation (error) means that in the sum over terms involving the differences $y_i - \Sigma_n w_{in} v_n$, every term is summed up with the same sign. In particular, the absolute density deviation (error) $f_j$ of the voxel under inspection may be calculated as the sum over squares of all differences for all x-ray projections 21, namely as $f_j = \Sigma_i (y_i - \Sigma_n w_{in} v_n)^2$. In this case, if the value of the sum $\Sigma_i$ is high, the confidence of the voxel under inspection is low, and vice versa. Alternatively, the absolute deviation (error) $f_j$ may for example be calculated by a sum over absolute differences for all x-ray projections 21, namely as $f_j = \Sigma_i |y_i - \Sigma_n w_{in} v_n|$. From the density error $f_j$, the probability $P_j$ that the density assigned to each voxel is correct may be calculated as $P_j = \exp(-f_j^2)$. In the above embodiment, the confidence measure may be derived from, or set equal to, the density error $f_j$ and/or the probability $P_j = \exp(-f_j^2)$ that the density assigned to each voxel is correct.

In another preferred embodiment, a-priori knowledge of the sample material is used in the calculation 24 of the confidence measures 28 in a voxel changing step 29 in which reconstructed voxels can be individually changed or manipulated in a predetermined manner. The forward projection 25 is then applied to the changed volume data 30 for generating artificial projections 26 of the sample 13. To compute confidence measures 28 for voxel elements of a given volume it may be necessary to repeat this step 24 iteratively many times, which is indicted by the arrow 34 in FIG. 3.

In a practical embodiment, this may be done in the following preferred manner. For each voxel j under consideration, the reconstructed density $v_j$ is successively replaced by a plurality of predefined densities $m_d$ in the voxel changing step 29. The hypothetical densities $m_d$ are typically densities which may be expected to be present in the sample 13, for example all pre-known material densities $m_d$ with d=1, 2, . . . , D which are known to be present in the sample; here, D is the number of materials known to be present in the sample. After the forward projection 25 for generating the corresponding artificial projections, in step 27, for each predefined density $m_d$ and for each x-ray which travels through the voxel j, i.e. for each x-ray projection of the set of real projections 21, the difference term $y_i - \Sigma_n w_{in} v_n + (w_{ij} v_j - w_{ij} v_d)$ is calculated, wherein the difference $(w_{ij} v_j - w_{ij} v_d)$ represents the voxel change as performed in step 29. The density error $f_j(m_d)$ may then be calculated from a sum over the terms $y_i - \Sigma_n w_{in} v_n + w_{ij} v_j - w_{ij} m_d$ summed up with the same sign, in particular the sum over the squared differences: $f_j = \Sigma_i (y_i - \Sigma_n w_{in} v_n + w_{ij} v_j - w_{ij} m_d)^2$. From the above it follows that it may be necessary to perform the steps 29, 30 and 25 to 27 many times iteratively.

The density error $f_j(m_d)$ may be converted into a probability $P_j(m_d) - \exp(-f_j^2)$ that the reconstructed density vj is equal to the corresponding predefined density $m_d$. The probability $P_j(m_d)$ is the larger the better the x-ray projections and/or the reconstructed data support the currently considered predefined density $m_d$. The probability $P_j(m_d)$ may be considered as a probability distribution 33 over the material density $m_d$. In the example of FIG. 4 probability distributions 33a, 33b corresponding to SART and SMART reconstructed data are shown. In the example of FIG. 4, four pre-defined material densities $m_d$ with d=1,2,3,4 have been tested, where in each case the four probabilities sum up to 1.0. It is evident that different reconstruction techniques may lead to substantially different results for the reconstructed material density. For example in FIG. 4 the density value 39a corresponding to the maximum of the probability distribution given by the SART technique would support the predefined density $v_j=m_2$ for the voxel j under inspection, whereas the density value 39b corresponding to the maximum of the probability distribution given by the SMART technique would support the predefined density $v_j=m_3$. Both distributions are relatively broad and have a relatively large variance $\sigma_j^2$ and a relatively low maximum probability $p_j^{max}$.

In the above embodiment, the confidence measure may preferably be derived from the probability distribution $P_j(m_d)$ over the predefined material densities $m_d$. For examples, the confidence measure may be taken as the maximum probability under all probabilities $P_j(m_d)$; the maximum probability $p_j^{max}$ of the continuous probability distribution; the variance $\sigma_j^2$; the standard deviation $\sigma$; full width at half maximum (FWHM); any other suited measure indicating how narrow or pronounced the maximum peak is in the distribution; and/or any suited combination of these. In particular, if for a particular voxel the (absolute) confidence value is small and the others are high, the confidence of that voxel is high. However, if all confidence values of the voxel under inspection are not too different within a given range, the confidence of that voxel is low. Generally, the smaller the variance of the confidence value distribution, the higher the support from the measurements and the better the quality of the calculated representations.

The entity of confidence measures of all voxels results in a confidence measure set 28 for the complete volume, of the sample 13. Therefore, a confidence measure set 28 of a reconstructed volume 23 comprises exactly as many confidence measure values as there are voxels in the reconstructed volume 23.

In other words, for every voxel in the reconstructed volume 23 two independent values result from the reconstruction process, for example in the form of grey values, namely one value giving the reconstructed material density of this voxel, and one value giving the confidence measure, i.e. the probability that the voxel density is correct. This means that two completely independent data sets are generated for the sample 13, namely the reconstructed volume data (density) 23 and the confidence measure data (density error) 28.

Advantageously, a resulting reconstructed volume data set 36 is calculated from the reconstructed volume data sets 23a, 23b in a data fusion step 35. This is preferably done in a voxel-by-voxel comparison and fusion, where a fusion criterion is evaluated for each single voxel of the reconstructed data volume. The fusion may be done in different ways. A preferred fusion method is based on the Dempster-Shafer-theory, where every reconstruction technique (SART, SMART, is interpreted as a sensor, the reconstructed densities of every voxel element is interpreted as a measurement, and the calculated confidence measures 28; 28a, 28b are used for quantifying the accuracy of every measurement as required for application of the Dempster-Shafer-theory. Alternatively, the density value of each resulting voxel may be calculated from the corresponding values of both sets 23a, 23b where a weight based on the respective confidence measure 28a, 28b is used to weight these values, such that the density value with the higher confidence measure 28a; 28b is given the higher weight. In another embodiment, the density value of each resulting voxel may be set to the corresponding value from the data set 23a, 23b which has the higher confidence measure 28a; 28b. Other suitable forms of deriving the resulting reconstructed volume data set 36 from the reconstructed volume data sets 23a, 23b are possible.

The Dempster-Shafer fused probability distribution 33c of the corresponding voxel $v_j$ is shown on the right side of FIG. 4. It is evident that the confidence measure of the resulting density value 39c of the voxel $v_j$ is higher, having a higher maximum probability $p_j^{max}$ and a more narrow distribution leading to a smaller variance $\sigma_j^2$ and standard deviation $\sigma$ as compared to the SART/SMART probability distributions shown on the left side of FIG. 4.

Preferably a set 37 of resulting confidence measures is calculated from both sets 28a, 28b of confidence measures. This is preferably done in a voxel-by-voxel comparison and fusion, where a fusion criterion is evaluated for each single voxel of the reconstructed data volume. The fusion may be done for example using an error propagation method, Dempster-Shafer theory, or any other suited method. In another example, for each voxel the higher confidence measure may be taken as the resulting confidence measure.

Preferably a set 38 of conflict measures is calculated for individual voxels of the sample volume indicating consistency conflicts between each first reconstructed voxel value and the corresponding second reconstructed voxel value. For example, the conflict measure of a voxel may be calculated to become high if the difference between the first and second voxel value is relatively large and both voxel values have a relatively high confidence measure. Regions of the reconstructed sample volume having a high conflict measure, for example a conflict measure exceeding a predetermined threshold, may be identified as critical regions which may require special attention or investigation. In particular, regions having a high conflict measure may preferably be displayed to an operator for example on the display means 43.

It is also possible to display, for example on the display device 43, voxels with different resulting confidence measures 37 by different optical indicators. In this manner the voxel confidence level can be directly indicated to an operator by an additional indicator like a colour coding, such that the quality of different parts in the reconstructed volume data or volume slices is immediately evident. In another embodiment for example voxels with a resulting confidence measure 37 corresponding to a confidence exceeding a predetermined threshold ("good voxels") and/or voxels with a resulting confidence measure 37 corresponding to a confidence falling below a predetermined threshold ("bad voxels") may be highlighted.

The CT method according to the invention and illustrated in FIGS. 2, 2a may be used in an automated defect recognition (ADR) system for non-destructive testing of industrial products, where an ADR algorithm is applied to the reconstructed volume data in order to determine defects in the sample under inspection. The ADR system may be realized by an ADR software in the computer apparatus 40. The resulting confidence measures 37 and/or conflict measures 38 of the sample volume may preferably be used in such an automated defect recognition (ADR) system, where the detection reliability can be significantly enhanced if the resulting confidence measures are used to distinguish defects from artefacts. In a further embodiment the quality information provided by the resulting confidence measures 37 and/or the conflict measures 38 can be fed back into the reconstruction process 22 (see FIG. 2) for improving the reconstruction quality or accuracy. In particular, the volume data reconstruction may be iteratively repeated with optimized parameters based on said resulting confidence measures 37 and/or conflict measures 38.

Still further advantageous applications of the invention relate to comparing the volume quality for different reconstruction parameters; and/or volume compression, where different volume regions of the reconstructed volume data can be compressed differently based on their quality as indicated by their resulting confidence measures 37 and/or conflict measures 38. In particular, regions having a relatively high conflict measure may advantageously be compressed stronger.

Calculation of a resulting reconstructed volume data 36 is not strictly necessary. In other words, calculating the resulting confidence measures 37 and/or the conflict measures 38 in the fusion step 35 may be beneficial on its own. Similarly, it is not strictly necessary to calculate both the resulting confidence measures 37 and the conflict measures 38, but calculating either of these may be sufficient.

In the embodiments shown in the Figures, two different volume data sets 23a, 23b are investigated. It goes without saying that the described CT method may be generalized to three or more different data sets 23a, 23b, 23c ( . . . ) originating for example from three or more different reconstruction techniques.

The CT method described in the present application is not restricted to rotatory trajectories. I.e., reconstructions from all possible CT trajectories, in particular also translational trajectories, may be evaluated and/or fused according to the teaching of the present application.

The invention claimed is:

1. A method of using computed tomography for determining a volumetric representation of a sample, the method comprising:
  receiving first x-ray projection data of the sample taken by an x-ray system;
  receiving second x-ray projection data of the sample taken by an x-ray system, wherein the first x-ray projection data is different from the second x-ray projection data;
  reconstructing first reconstructed volume data of the sample from the first x-ray projection data, the first reconstructed volume data including a first voxel representing a region of the sample;
  reconstructing second reconstructed volume data of the sample from the second x-ray projection data, the second reconstructed volume data including a second voxel representing the region of the sample;
  calculating first individual confidence measures of each corresponding single voxel from the first reconstructed volume data, the first individual confidence measures including a first confidence measure associated with the first voxel;
  calculating second individual confidence measures of each corresponding single voxel from the second reconstructed volume data, the second individual confidence measures including a second confidence measure associated with the second voxel; and
  combining the first reconstructed volume data and the second reconstructed volume data by voxel-by-voxel comparison and fusion, wherein a fusion criterion is evaluated for each single voxel of the reconstructed data volume based at least partially upon the first individual confidence measures and the second individual confidence measures, the voxel-by-voxel comparison including comparing the first confidence measure and the second confidence measure to evaluate the fusion criterion, and the fusion including selecting either of the first voxel or the second voxel based at least partially upon the first confidence measure and the second confidence measure.

2. The method according to claim 1, further comprising calculating a conflict measure for individual voxels of the sample volume from the first individual confidence measures and the second individual confidence measures.

3. The method according to claim 1, further comprising generating resulting reconstructed volume data from the first reconstructed volume data and the second reconstructed volume data based on the first individual confidence measures and the second individual confidence measures.

4. The method according to claim 3, wherein generating resulting reconstructed volume data comprises generating reconstructed volume data based on Dempster-Shafer-theory.

5. The method according to claim 1, wherein calculating an individual resulting confidence measure comprises calculating an individual resulting confidence measure based on Dempster-Shafer-theory.

6. The method according to claim 1, wherein reconstructing first reconstructed volume data comprises reconstructing first reconstructed volume data via a first reconstruction method, wherein reconstructing second reconstructed volume data comprises reconstructing second reconstructed volume data via a second reconstruction method, wherein the second reconstruction method is different from the first reconstruction method.

7. The method according to claim 1, wherein reconstructing first reconstructed volume data comprises reconstructing first reconstructed volume data via a first reconstruction method with a first parameter set, wherein reconstructing second reconstructed volume data comprises reconstructing second reconstructed volume data via a second reconstruction method with a second parameter set, wherein the second parameter set is different from the first parameter set.

8. The method according to claim 1, wherein reconstructing first reconstructed volume data comprises reconstructing first reconstructed volume data via a first reconstruction method, wherein reconstructing second reconstructed volume data comprises reconstructing second reconstructed volume data via a second reconstruction method, wherein the second reconstruction method is identical to the first reconstruction method.

9. The method according to claim 1, wherein the first individual confidence measures are calculated essentially from the first x-ray projection data and the first reconstructed volume data and the second individual confidence measures are calculated essentially from the second x-ray projection data and the second reconstructed volume data.

10. One or more non-transitory computer-readable media having computer-usable instructions embodied thereon for performing operations for using computed tomography for determining a volumetric representation of a sample, the operations comprising:
  receiving first x-ray projection data of the sample taken by an x-ray system;

receiving second x-ray projection data of the sample taken by an x-ray system, wherein the first x-ray projection data is different from the second x-ray projection data;

reconstructing first reconstructed volume data of the sample from the first x-ray projection data, the first reconstructed volume data including a first voxel representing a region of the sample;

reconstructing second reconstructed volume data of the sample from the second x-ray projection data, the second reconstructed volume data including a second voxel representing the region of the sample;

calculating first individual confidence measures of each corresponding single voxel from first reconstructed volume data, the first individual confidence measures including a first confidence measure associated with the first voxel;

calculating second individual confidence measures of each corresponding single voxel from the second reconstructed volume data, the second individual confidence measures including a second confidence measure associated with the second voxel; and combining the first reconstructed volume data and the second reconstructed volume data by voxel-by-voxel comparison and fusion, wherein a fusion criterion is evaluated for each single voxel of the reconstructed data volume based at least partially upon the first individual confidence measures and the second individual confidence measures, the voxel-by-voxel comparison including comparing the first confidence measure and the second confidence measure to evaluate the fusion criterion, and the fusion including selecting either of the first voxel or the second voxel based at least partially upon the first confidence measure and the second confidence measure.

11. A computing device, programmed in a non-transitory manner, with instructions for performing operations for using computed tomography for determining a volumetric representation of a sample, the operations comprising:

receiving first x-ray projection data of the sample taken by an x-ray system;

receiving second x-ray projection data of the sample taken by an x-ray system, wherein the first x-ray projection data is different from the second x-ray projection data;

reconstructing first reconstructed volume data of the sample from the first x-ray projection data, the first reconstructed volume data including a first voxel representing a region of the sample;

reconstructing second reconstructed volume data of the sample from the second x-ray projection data, the second reconstructed volume data including a second voxel representing the region of the sample;

calculating first individual confidence measures of each corresponding single voxel from the first reconstructed volume data, the first individual confidence measures including a first confidence measure associated with the first voxel;

calculating second individual confidence measures of each corresponding single voxel from the second reconstructed volume data, the second individual confidence measures including a second confidence measure associated with the second voxel; and combining the first reconstructed volume data and the second reconstructed volume data by voxel-by-voxel comparison and fusion, wherein a fusion criterion is evaluated for each single voxel of the reconstructed data volume based at least partially upon the first individual confidence measures and the second individual confidence measures, the voxel-by-voxel comparison including comparing the first confidence measure and the second confidence measure to evaluate the fusion criterion, and the fusion including selecting either of the first voxel or the second voxel based at least partially upon the first confidence measure and the second confidence measure.

12. A computed tomography system, comprising:

an x-ray system adapted to take a set of x-ray projections of a sample, and a computing device adapted for using computed tomography for determining a volumetric representation of a sample, the computing device adapted to perform operations comprising:

receiving first x-ray projection data of the sample taken by an x-ray system;

receiving second x-ray projection data of the sample taken by an x-ray system, wherein the first x-ray projection data is different from the second x-ray projection data;

reconstructing first reconstructed volume data of the sample from the first x-ray projection data, the first reconstructed volume data including a first voxel representing a region of the sample;

reconstructing second reconstructed volume data of the sample from the second x-ray projection data, the second reconstructed volume data including a second voxel representing the region of the sample;

calculating first individual confidence measures of each corresponding single voxel from the first reconstructed volume data, the first individual confidence measures including a first confidence measure associated with the first voxel;

calculating second individual confidence measures of each corresponding single voxel from the second reconstructed volume data, the second individual confidence measures including a second confidence measure associated with the second voxel; and calculating at least one resulting set of individual values for each voxel based on said first individual confidence measures and said second individual confidence measures, said individual values comprising:

reconstructed volume data generated from said first and second reconstructed volume data based on said first and second individual confidence measures in a fusion step, an individual resulting confidence measure generated from said first and second individual confidence measures, and a conflict measure calculated for individual voxels of the sample volume generated from said first and second individual confidence measures, wherein the fusion step comprises a voxel-by-voxel comparison and fusion, wherein a fusion criterion is evaluated for each single voxel of the reconstructed data volume, the voxel-by-voxel comparison including comparing the first confidence measure and the second confidence measure to evaluate the fusion criterion, and the fusion including selecting either of the first voxel or the second voxel based at least partially upon the first confidence measure and the second confidence measure.

* * * * *